United States Patent [19]

Plyley et al.

[11] Patent Number: 5,630,539

[45] Date of Patent: May 20, 1997

[54] LAPAROSCOPIC STAPLER WITH OVERLOAD SENSOR AND INTERLOCK

[75] Inventors: Alan K. Plyley; Claude A. Vidal, both of Santa Barbara; Roger Lagerquist, Isla Vista, all of Calif.

[73] Assignee: United States Surgical Corporation, Norwalk, Conn.

[21] Appl. No.: 565,631

[22] Filed: Nov. 27, 1995

Related U.S. Application Data

[63] Continuation of Ser. No. 237,004, May 2, 1994, Pat. No. 5,470,007.

[51] Int. Cl.$^6$ .................................................. A61B 17/068
[52] U.S. Cl. ........................ 227/175.1; 227/19; 227/175.2; 227/176.1
[58] Field of Search ........................ 227/19, 175.1, 227/176.1, 178.1, 175.2, 175.3

[56] References Cited

U.S. PATENT DOCUMENTS

| | | |
|---|---|---|
| 2,174,219 | 9/1939 | Balma . |
| 2,246,647 | 6/1941 | Vancura . |
| 3,079,606 | 3/1963 | Bobrov et al. . |
| 3,490,675 | 1/1970 | Green et al. . |
| 3,499,591 | 3/1970 | Green . |
| 3,601,302 | 8/1971 | Potekhina et al. ................ 227/19 |
| 3,692,224 | 9/1972 | Astafiev et al. . |
| 3,844,289 | 10/1974 | Noiles . |
| 4,086,926 | 5/1978 | Green et al. . |
| 4,202,480 | 5/1980 | Annett . |
| 4,256,251 | 3/1981 | Moshofsky . |
| 4,304,236 | 12/1981 | Conta et al. . |
| 4,383,634 | 5/1983 | Green ................................... 227/19 |
| 4,391,401 | 7/1983 | Moshofsky . |
| 4,415,112 | 11/1983 | Green . |
| 4,473,077 | 9/1984 | Noiles et al. . |
| 4,519,532 | 5/1985 | Foslien . |
| 4,520,817 | 6/1985 | Green . |
| 4,527,724 | 7/1985 | Chow et al. . |
| 4,569,346 | 2/1986 | Poirier . |
| 4,576,167 | 3/1986 | Noiles . |
| 4,591,085 | 5/1986 | DiGiovanni . |
| 4,596,350 | 6/1986 | Smith et al. ........................ 227/19 |
| 4,607,636 | 8/1986 | Kula et al. . |
| 4,608,981 | 9/1986 | Rothfuss et al. . |
| 4,633,861 | 1/1987 | Chow et al. . |
| 4,633,874 | 1/1987 | Chow et al. . |
| 4,646,745 | 3/1987 | Noiles . |
| 4,664,305 | 5/1987 | Blake, III et al. . |
| 4,671,445 | 6/1987 | Barker et al. . |
| 4,754,909 | 7/1988 | Barker et al. . |
| 4,809,898 | 3/1989 | Gassner et al. . |
| 4,863,088 | 9/1989 | Redmond et al. . |
| 4,869,415 | 9/1989 | Fox . |
| 4,892,244 | 1/1990 | Fox et al. . |
| 4,938,408 | 7/1990 | Bedi et al. . |
| 4,955,959 | 9/1990 | Tompkins et al. . |
| 5,031,814 | 7/1991 | Tompkins et al. . |
| 5,040,715 | 8/1991 | Green et al. . |
| 5,071,052 | 12/1991 | Rodak et al. . |
| 5,106,008 | 4/1992 | Tompkins et al. . |
| 5,116,349 | 5/1992 | Aranyi . |
| 5,397,046 | 3/1995 | Savage et al. . |
| 5,413,267 | 5/1995 | Solyntjes et al. ................ 227/19 |
| 5,439,468 | 8/1995 | Schulze et al. ................... 227/19 |
| 5,470,007 | 11/1995 | Plyley et al. . |
| B1 4,892,244 | 8/1991 | Fox et al. . |

FOREIGN PATENT DOCUMENTS

| | | |
|---|---|---|
| 0484677 | 5/1992 | European Pat. Off. . |
| 0552423 | 7/1993 | European Pat. Off. . |
| 0593920 | 4/1994 | European Pat. Off. . |
| 2437820 | 6/1979 | France . |

*Primary Examiner*—Scott A. Smith

[57] ABSTRACT

A surgical stapler with an overload sensor and lockout is disclosed. The surgical stapler is particularly useful in laparoscopic surgical procedures.

9 Claims, 3 Drawing Sheets

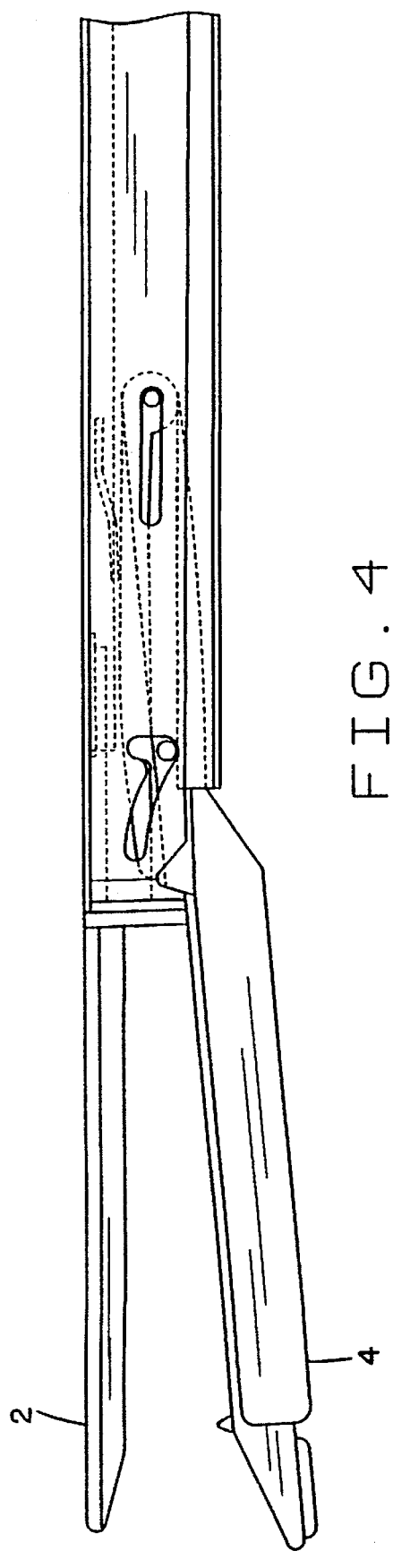
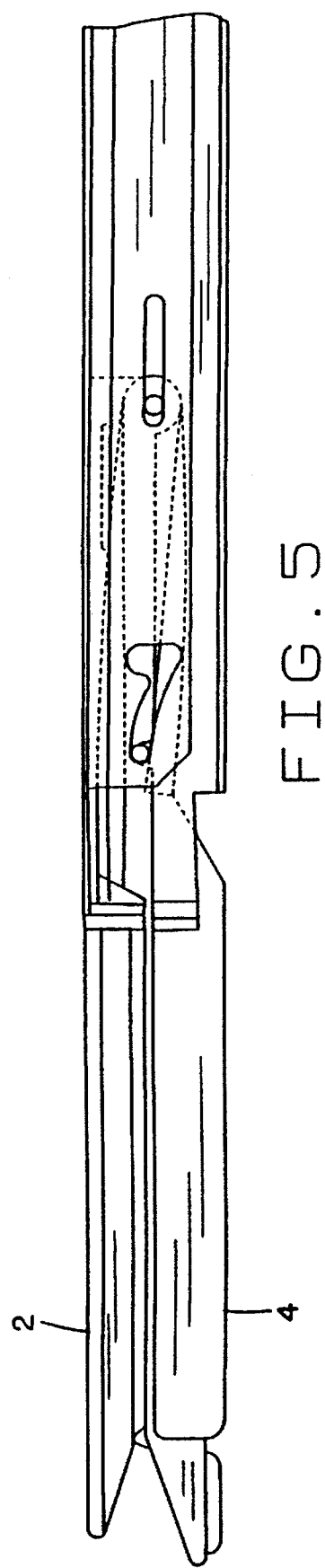
FIG. 4
FIG. 5

LAPAROSCOPIC STAPLER WITH OVERLOAD SENSOR AND INTERLOCK

This application is a continuation application of U.S. application Ser. No. 08/237,004, filed May 2, 1994, now U.S. Pat. No. 5,470,007.

BACKGROUND

This invention relates to laparoscopic staplers, and in particular to an overload sensor and lockout for laparoscopic staplers.

Laparoscopic surgical techniques have greatly reduced the trauma and risks associated with certain surgeries, and have expedited patient recovery and reduced scarring. However, laparoscopic surgical techniques also present many challenges to the surgeon. The surgeon must perform delicate procedures with a limited view of the surgical site. The surgeon is separated from the surgical field, and cannot always rely on the sense of touch. One area that can be particularly challenging is in the use of laparoscopic staplers. These staplers typically include jaws which gather or approximate the tissues to be stapled, and a staple forming apparatus which forms a staple in the tissues approximated in the jaws. An example of such a stapler is disclosed in Green et al., U.S. Pat. No. 5,040,715, incorporated herein by reference. In using laparoscopic staplers, the surgeon does not have an ideal, three dimensional view of the tissues being stapled as compared to some open surgical techniques, and receives only limited tactile feedback of the tissues being approximated in the jaws by the operation of the instrument. Thus, it is possible for the surgeon to occasionally gather excessive tissue between the jaws of the stapler. If there is excessive tissue between the jaws, there is a risk that the stapler could be damaged, or that if a staple is placed it will not be properly formed or will not adequately hold the tissue. Thus, the surgeon must proceed slowly and deliberately to anticipate the potential for approximating an excess quantity of tissue between the jaws of the stapler.

BRIEF DESCRIPTION OF THE INVENTION

The present invention relates to a laparoscopic stapler with an overload sensor that interrupts the operation of the jaws and/or prevents the placement of a staple if more than a predetermined amount of tissue has been approximated between the jaws. This overload sensor allows the surgeon to proceed faster with the stapling operation, since the surgeon does not have to rely solely on the limited visual and tactile feedback available.

Generally the laparoscopic stapler of this invention comprises jaws which close together to approximate the tissues to be stapled and a linkage operable to close the jaws. At least a portion of the linkage is movable, in response to a load between the jaws, out of its normal operating position so that normal operation of the linkage is interrupted. A spring resiliently biases the movable portion of the linkage to its normal operating position, and holds the movable portion of the linkage in its normal operating position as the linkage closes the jaws on no more than a predetermined appropriate amount of tissue. However the spring allows the movable portion of the linkage to move from its normal operating position as the linkage closes the jaws on more than the predetermined appropriate amount of tissue so that normal operation of the linkage will be interrupted.

In the preferred embodiment, the laparoscopic stapler also includes an interlock that prevents a staple from being formed when there is more than a predetermined amount of tissue between the jaws. The preferred embodiment of the laparoscopic stapler comprises jaws which close together to approximate the tissues to be stapled, and a linkage operable to close the jaws. The stapler also includes a staple forming apparatus and a trigger for actuating the staple forming apparatus to form a staple in the tissues approximated in the jaws. At least a portion of the linkage is movable, in response to a load between the jaws, out of its normal operating position so that normal operation of the linkage is interrupted. A spring resiliently biases the movable portion of the linkage to its normal operating position, and holds the movable portion of the linkage in its normal operating position as the linkage closes the jaws on no more than a predetermined appropriate amount of tissue. However, the spring allows the movable portion of the linkage to move from its normal operating position as the linkage closes the jaws on more than the predetermined appropriate amount of tissue so that normal operation of the linkage will be interrupted. An interlock, releasable upon the normal operation of the linkage, engages the trigger and prevents the actuation of the staple forming apparatus until released.

Thus, the laparoscopic stapler of the present invention helps to reduce the chance that the surgeon will close the jaws on an inappropriate amount of tissue, and in the preferred embodiment reduces the chance that the surgeon will attempt to place a staple in an inappropriate amount of tissue. This reduces the risk of improper staple formation or placement, and reduces the risk of damage to the stapling equipment. These and other features and advantages will be in part apparent, and in part pointed out hereinafter.

BRIEF DESCRIPTION OF THE DRAWINGS

FIG. 4 is a side elevation view of the distal end of the stapler with the jaws open, corresponding to the handle position of FIG. 1; and FIG. 5 is a side elevation view of the distal end of the stapler with the jaws closed, corresponding to the handle position of FIG. 2.

Corresponding reference numerals indicate corresponding parts throughout the drawings.

DETAILED DESCRIPTION OF THE PREFERRED EMBODIMENT

Figure 1:
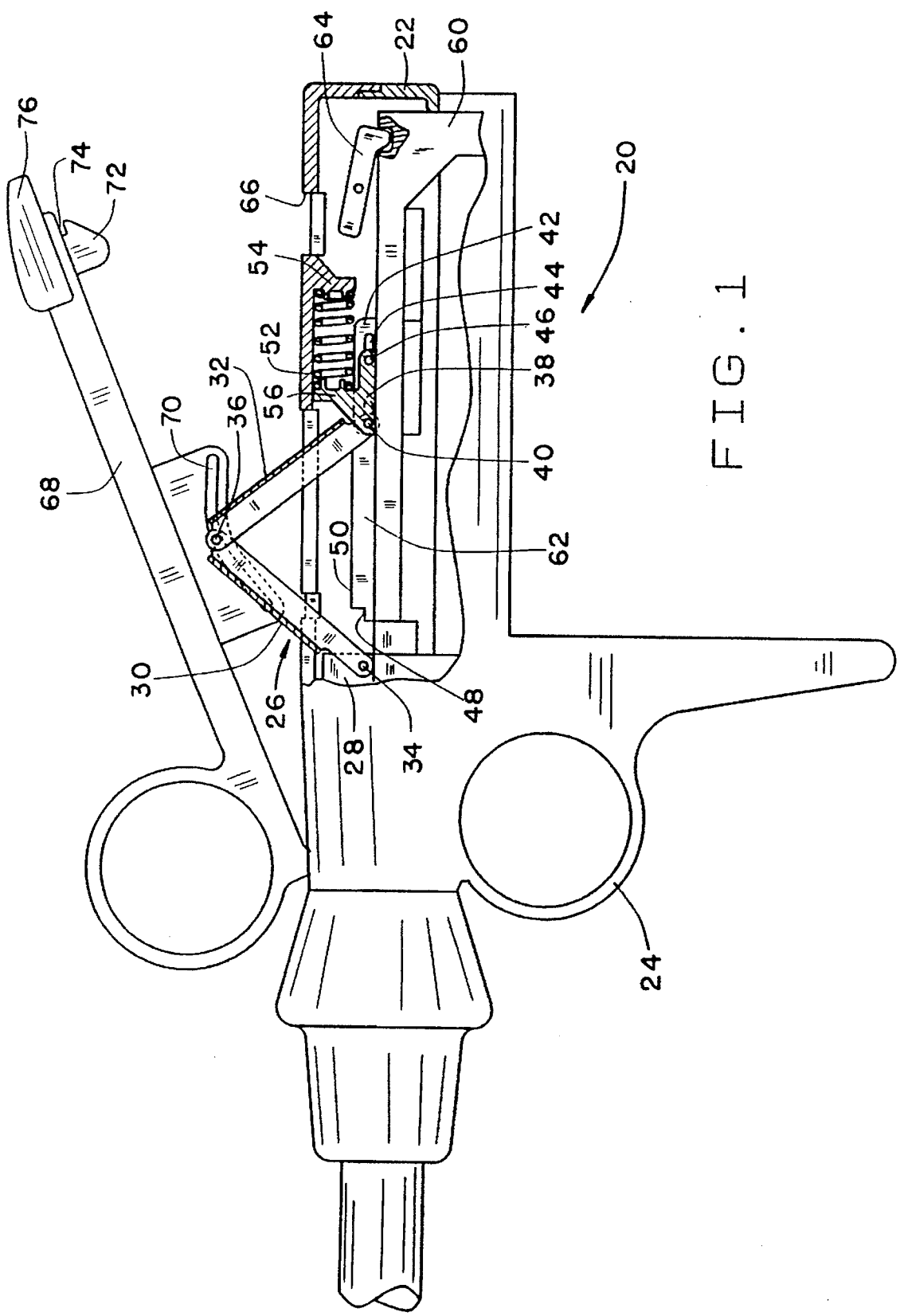
FIG. 1 is a longitudinal cross-sectional view of the proximal end of a laparoscopic stapler constructed according to the principles of this invention, with the linkage in the normal operating position with the jaws open.

The proximal end of laparoscopic stapler with overload sensor constructed according to the principles of this invention is indicated generally as 20 in FIG. 1. The end of the stapler comprises a housing 22, including a finger ring 24 for the user to grasp the stapler. The stapler has a pair of jaws 2 and 4 (see FIGS. 4 and 5) which gather or approximate the tissues to be stapled. The jaws 2 and 4 are shown in their open position in FIG. 4, corresponding to the handle position shown in FIG. 1. The jaws 2 and 4 are shown in their closed position in FIG. 5, corresponding to the handle position shown in FIG. 2. The stapler also includes a staple forming apparatus which forms a staple in the tissues approximated in the jaws 2 and 4. For example, the stapler may include the staple forming apparatus and/or other features of the staplers disclosed in commonly assigned U.S. patent application Ser. No. 08/236,379, now U.S. Pat. No. 5,489,058 filed on the same day as the present application in the name of Alan K. Plyley, Claude A. Vidal, Russell J. Redmond, John Minck, Jr. and Alan J. Solyntjes, the entire contents of which are herein expressly incorporated by reference.

The stapler also includes a linkage 26 operable to close the jaws 2 and 4. The linkage preferably includes member 28, and links 30 and 32. The distal end of the link 30 is pivotally connected to the member 28 with forward toggle pin 34. The proximal end of the link 30 and the distal end of the link 32 are pivotally connected with a center toggle pin 36. The proximal end of the link 32 is pivotally connected to base 38 with rear toggle pin 40. Operation of the linkage by the movement of the center toggle pin inwardly toward the housing 22 causes the jaws 2 and 4 to close.

Figure 2:
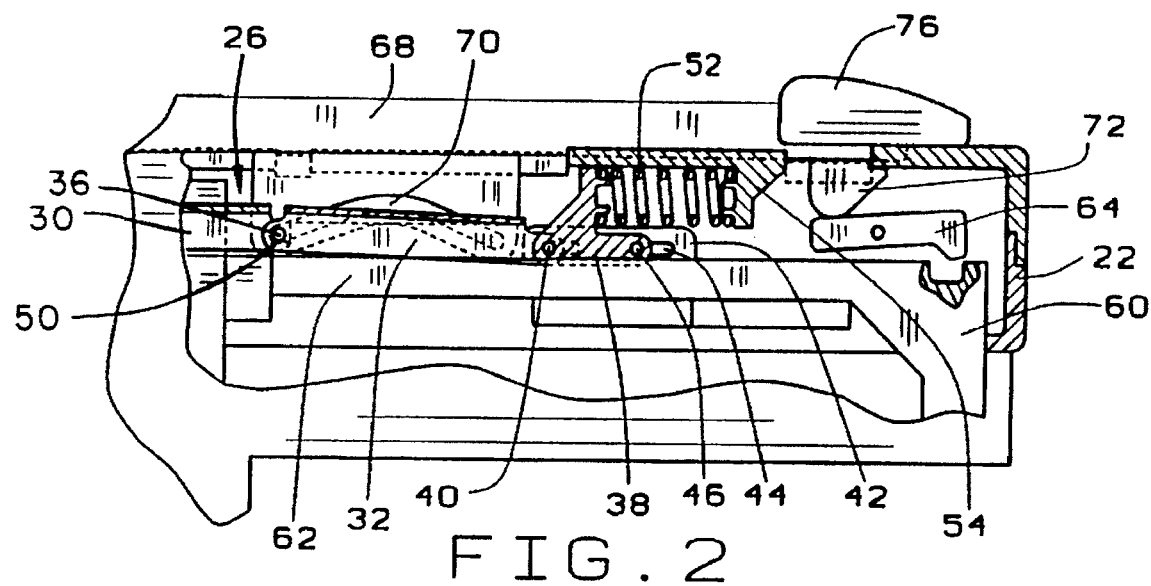
FIG. 2 is a longitudinal cross-sectional view of the proximal end of the laparoscopic stapler, with the linkage in the normal operating position with the jaws closed.

According to the principles of this invention, a portion of the linkage 26 is preferably movable in response to a load between the jaws 2 and 4. In this preferred embodiment, the base 38, which pivotally supports the proximal end of the link 32, is slidable inside the housing 22. A support 42, having a longitudinally extending slot 44 therein, is provided inside the housing 22. The base 38 has a pin 46 that is received in the slot 44 in the support 42 to limit the proximal and distal movement of the base 38. When the linkage 26 is in its normal operating position, the links 30 and 32 can move inwardly until the center toggle pin 36 connecting the links engages the normal stop 48. This occurs when the base 38 is in its distal-most position as shown in FIGS. 1 and 2. However, when the linkage 26 is not in its normal operating position, the links 30 and 32 can only move inwardly until the pin engages the stop 50. This occurs when the base 38 slides proximally, which allows the proximal end of the link 32 to slide proximally. The stop 50 interferes with the operation of the linkage 26. Moreover, the proximal movement of the proximal end of the link 32 reduces the net amount of distal movement of the distal end of the link 30, thereby reducing the amount the jaws 2 and 4 are closed.

Figure 3:
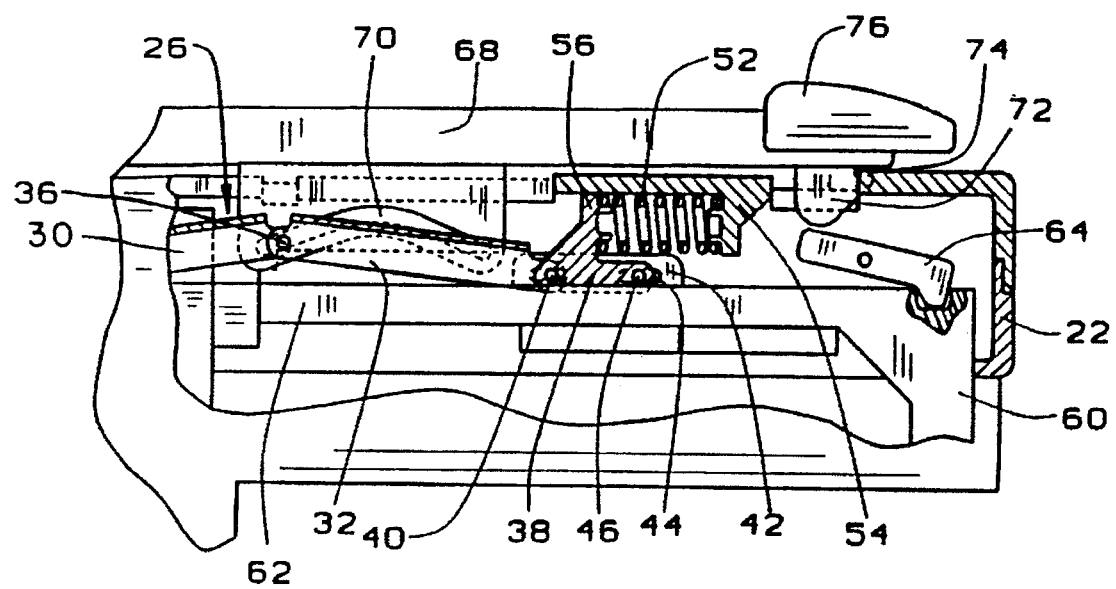
FIG. 3 is a longitudinal cross-sectional view of the proximal end of the laparoscopic stapler, with the linkage out of its normal operating position as would occur from an overload between the jaws.

Thus, when the linkage 26 remains in its normal operating position, the linkage operates as shown in FIG. 2, and closes the jaws 2 and 4, as shown in FIG. 5. However, when the linkage 26 moves from its normal operating position, the stop 50 interferes with the operation of the linkage, interrupting the linkage as shown in FIG. 3, and preventing the jaws 2 and 4 from completely closing.

The stapler also comprises a spring 52 that extends between an anchor 54 on the housing 22, and an anchor 56 on the base 38. The spring 52 resiliently biases the linkage 26 to its normal operating position, by resiliently biasing the base 38 distally. The spring 52 is sized to hold the linkage 26 in its normal operating position as the linkage 26 closes the jaws 2 and 4 on no more than a predetermined appropriate amount of tissue. However, the spring 52 is also sized to allow a portion of the linkage 26 to move from its normal operating position as the linkage 26 closes the jaws 2 and 4 on more than the predetermined appropriate amount of tissue so that normal operation of the linkage 26 is interrupted.

The stapler preferably includes a trigger 60 for actuating the staple forming apparatus to form a staple in the tissues approximated in the jaws 2 and 4. The trigger is connected by a trigger shaft 62 to the staple forming apparatus. The trigger 60 is operated distally relative to the housing 22 to actuate the staple forming device.

An interlock 64, releasable upon the normal operation of the linkage 26, engages the trigger 60 and prevents the actuation of the staple forming apparatus until the interlock 64 is released. The interlock 64 is preferably pivotally mounted in the housing for movement between a locked position in which the interlock 64 engages the trigger 60, and an unlocked position in which the interlock 64 is spaced from the trigger 60. A portion of the interlock 64 is exposed through a window 66 in the housing 22.

In this preferred embodiment, the stapler also includes a handle or grip 68, pivotally mounted to the housing 22. The grip includes an arcuate slot 70 which receive the center toggle pin 36, so that the pivoting of the grip 68 toward the housing 22 operates the linkage 26 to cause the jaws 2 and 4 to close. The grip 68 also has a tang 72, that is adapted to fit through the window 66 in the housing 22, and releasably hold the grip against the housing 22 to hold the jaws 2 and 4 closed. The tang 72 has a notch 74 to engage the marginal edge of the window 66. The tang 72 projects sufficiently through the window 60 in the housing 22 to pivot the interlock 64. When the linkage 26 operates normally, the grip 68 can pivot to a position against the housing 22 so that the tang 72 pivots the interlock 64 to release it from the trigger 60. However, when the linkage 26 does not operate normally, as occurs when there is too much tissue between the jaws 2 and 4, the linkage 26 prevents the grip 68 from pivoting against the housing 22, and thus prevents the tang 72 from extending sufficiently through the window 66 to pivot the interlock 64, thereby leaving the trigger 60 locked. The grip 68 can be released from its locked position against the housing 22 by sliding knob 76, which causes the notch 74 or tang 72 to disengage from the window 66.

OPERATION

The operation of the stapler is readily understood. The operator manipulates the stapler into position, and closes the jaws 2 and 4 by squeezing the grip 68 to operate the linkage 26. If there is no more than a predetermined amount of tissue between the jaws 2 and 4, the linkage 26 will operate normally, with the links 30 and 32 pivoting until the center toggle pin 36 abuts the stop 48. The tang 72 on the grip 68 extends through the window 66 to engage the margins of the window 66, thereby locking the jaws 2 and 4. The tang 72 also pivots the interlock 64 to its unlocked position so that the operator can move the trigger 60 forward to actuate the staple forming apparatus. See FIG. 2.

If there is more than the predetermined amount of tissue between the jaws 2 and 4, then the force caused by the attempt to close the jaws 2 and 4 causes the base 38 to slide proximally against the force of the spring 52, bringing the linkage 26 out of its normal operating position. The links 30 and 32 pivot until the center toggle pin 36 abuts the stop 52. In this position, the jaws 2 and 4 are not fully closed, reducing the overloading of the stapler. Furthermore, the grip 68 cannot pivot sufficiently close to the housing for the tang 72 to penetrate sufficiently through the window 66 to release the interlock 64. Thus, the trigger 60 is locked from actuating the staple former, reducing the risk of a malformed or improperly placed staple.

Thus, the laparoscopic stapler of the present invention helps to reduce overloading of the stapler and reduces the risk of malformed or improperly placed staples.

What is claimed is:

1. A surgical stapler comprising:
   (a) a housing;
   (b) an elongated shaft, defining a longitudinal axis, mounted to said housing;
   (c) first and second jaws mounted with respect to said elongated shaft, said first and second jaws being movable with respect to each other so as to receive tissue therebetween;
   (d) an approximating handle movably mounted with respect to said housing; and
   (e) an assembly having proximal and distal ends and an intermediate portion, said assembly movably mounted with respect to said elongated shaft and operatively connected to said approximating handle at said intermediate portion and to at least one of said first and second jaws at said distal end, said intermediate portion adapted to move inwardly with respect to said longitudinal axis to a first position and further adapted to move to a second position longitudinally offset from said first position in response to a preselected stimulus exerted on at least one of said first and second jaws.

2. The surgical stapler of claim 1, wherein said approximating handle is pivotally mounted to said housing.

3. The surgical stapler of claim 1, wherein said approximating handle defines a cam slot and said assembly includes a member at said intermediate portion movably positioned within said cam slot.

4. The surgical stapler of claim 1, further comprising a spring member mounted with respect to said proximal end of said assembly and biasing said proximal end against longitudinal movement.

5. The surgical stapler of claim 1, wherein said assembly includes at least two links.

6. The surgical stapler of claim 1, wherein said preselected stimulus includes a thickness of tissue in excess of that compatible with a staple mounted in one of said first and second jaws.

7. The surgical stapler of claim 1, wherein said handle is blocked from inward movement when said intermediate portion is in said second position.

8. The surgical stapler of claim 1, further comprising a trigger movably mounted to said housing, said trigger actuating a staple forming apparatus operatively associated with the first and second jaws.

9. The surgical stapler of claim 1, wherein said trigger is blocked from movement in said second position.

* * * * *